US00PP37368P2

(12) United States Plant Patent
Gerbac

(10) Patent No.: US PP37,368 P2
(45) Date of Patent: Apr. 14, 2026

(54) GRAPEVINE PLANT NAMED 'KE-wz1'

(50) Latin Name: ***Vitis vinifera* hybrid**
Varietal Denomination: KE-wz1

(71) Applicant: Kangaru Enterprises, LLC, Solvang, CA (US)

(72) Inventor: Steven Gerbac, Solvang, CA (US)

(73) Assignee: Kangaru Enterprises, LLC, Solvang, CA (US)

( * ) Notice: Subject to any disclaimer, the term of this patent is extended or adjusted under 35 U.S.C. 154(b) by 0 days.

(21) Appl. No.: 19/075,188

(22) Filed: Mar. 10, 2025

(51) Int. Cl.
*A01H 5/08* (2018.01)
*A01H 6/88* (2018.01)

(52) U.S. Cl.
USPC ..... Plt./207

(58) Field of Classification Search
USPC ..... Plt./157, 205, 207
See application file for complete search history.

(56) References Cited

U.S. PATENT DOCUMENTS

| | | | | |
|---|---|---|---|---|
| PP29,847 | P2 * | 11/2018 | Hemstad | Plt./207 |
| PP33,282 | P3 * | 7/2021 | Juneau | A01H 6/88 Plt./206 |
| 2025/0081869 | P1 * | 3/2025 | Bourne | A01H 6/88 Plt./207 |

* cited by examiner

*Primary Examiner* — Karen M Redden
(74) *Attorney, Agent, or Firm* — Stefan J. Kirchanski; Zuber Lawler LLP

(57) ABSTRACT

The invention is a new and distinct variety of grapevine plant named 'KE-wz1', which is vegetatively identical to 'Zinfandel' (not patented) but is characterized by white fruit with high acidity and distinctive aromatic characteristics suitable for producing improved white Zinfandel wine and premium white wines.

4 Drawing Sheets

Genus and species: *Vitis vinifera* hybrid.
Variety denomination: 'KE-wz1'.

CROSS-REFERENCE TO PRIOR APPLICATIONS

N/A

U.S. GOVERNMENT SUPPORT

N/A

BACKGROUND OF THE INVENTION

Grapes are the fruits of deciduous vines of the botanical genus *Vitis*. Grapes can be consumed as fresh fruit (table grapes) or they can be used to create a wide variety of food products, the most important being fermented grape juice—AKA 'wine'. California is one of the world's major wine producers. The story of wine production in California is long and interesting. The Spanish missionaries in the 18th century recognized that the Californian climate was ideal for wine production, but it was not until the 19th century that the suitability of California for the production of fine wines was recognized. An early pioneer in this effort was Agoston Haraszthy, a Hungarian nobleman who first tried to establish European wine grapes on Long Island, NY where the climate proved inhospitable for European grapes. His second attempt was in Wisconsin where some of his efforts still survive. Finally, he moved his operations to Sonoma, CA where he established California fine wine production. He introduced cuttings of many of the fine European wine varietals to California. This proved to be extremely fortuitous for the history of American as well as European viticulture. When a majority of the European vineyards were wiped out by phylloxera, it was cuttings from Haraszthy's vineyards that were used to reestablish many of the European vineyards.

One of the quintessential grape varieties in California is the red variety known as 'Zinfandel' (not patented). Although it was suspected that this variety was introduced by Haraszthy, it could not be assigned to one of the European varieties, so it was long assumed to be a hybrid originating in California. It was only with the advent of DNA genotyping that it was established that 'Zinfandel' is identical to the Croatian variety 'Crljenak Kastelanski' (not patented) which was also transplanted to Italy at about the same time it was taken to California. In Italy, the grape is known as 'Primativo' (not patented). As is understood by viticulturalists and enologists, clonal selection of grape varieties results in propagation of subtle somaclonal variations, so that a typical 'Zinfandel' vine in California may be subtly different from 'Primativo' or 'Crljenak Kastelanski'. Therefore, the present inventor was excited to find ancient 'Zinfandel' vines growing on Santa Cruz Island, one of the Channel Islands off the coast of Southern California. These vines were planted in the 19th century and have been long isolated from other vineyards and are, hence, believed to be close to the original 'Zinfandel' clone introduced into California in the 19th century.

'Zinfandel' is a red grape that produces a dark and intense red wine. It has a long history of use in various Californian red wine blends. More recently, "white zinfandel" wine has been produced by removing the seeds and skins from the wine must before fermentation has taken place. Often, "white zinfandel" wine is sweet and relatively bland because it contains few tannins and flavor elements from the grape skins. Therefore, there is a considerable need for a Zinfandel grape with little or no skin coloring. This would allow production of "white zinfandel" with an improved taste profile.

SUMMARY OF THE INVENTION

The present invention relates to a new and distinct grape cultivar named 'KE-wz1' that was grown from 'Zinfandel' seeds planted in 2014. These seeds resulted from open pollination of the Channel Island 'Zinfandel' vines mentioned above. Genetic testing has confirmed that the pollen as well as the seed parents of the new cultivar were 'Zinfandel'. It was considered that the long isolation of the parent plants on the Santa Rosa Island might have allowed interesting mutations to accumulate in the plants. The inventor was surprised and pleased to discover that several of the vines growing from the planted seeds produced white fruit (i.e., the skins are essentially colorless, allowing the green or yellowish flesh of the berries to show through). Otherwise, the vegetative characteristics of these seedlings were similar or identical to ordinary 'Zinfandel'. Namely, the vine is characterized by medium to large, deeply five-lobed leaves with prominent triangular teeth, dense hairs on the underside, and produces conical clusters of berries that often have a visible stylar scar. The seedling having the most favorable fruit color and vegetative vigor was selected as the new cultivar 'KE-wz1'. That vine was asexually propagated from hardwood cuttings. The asexually propagated plants were grown at Rusack Vineyards in Santa Barbara County, California. The propagated plants show no significant variation and are identical to the originally selected 'KE-wz1' cultivar. The characteristics and distinctions of this cultivar came true to form and were stable over succeeding generations of asexual reproduction.

DESCRIPTION OF THE FIGURES

The new grapevine cultivar 'KE-wz1' is illustrated by the accompanying photographs. The colors of these illustrations may vary with lighting conditions and, therefore, color characteristics of this new cultivar should be determined with reference to the observations described herein, rather than from these illustrations alone. These samples were photographed in mid-August.

DETAILED DESCRIPTION

Figure 1:
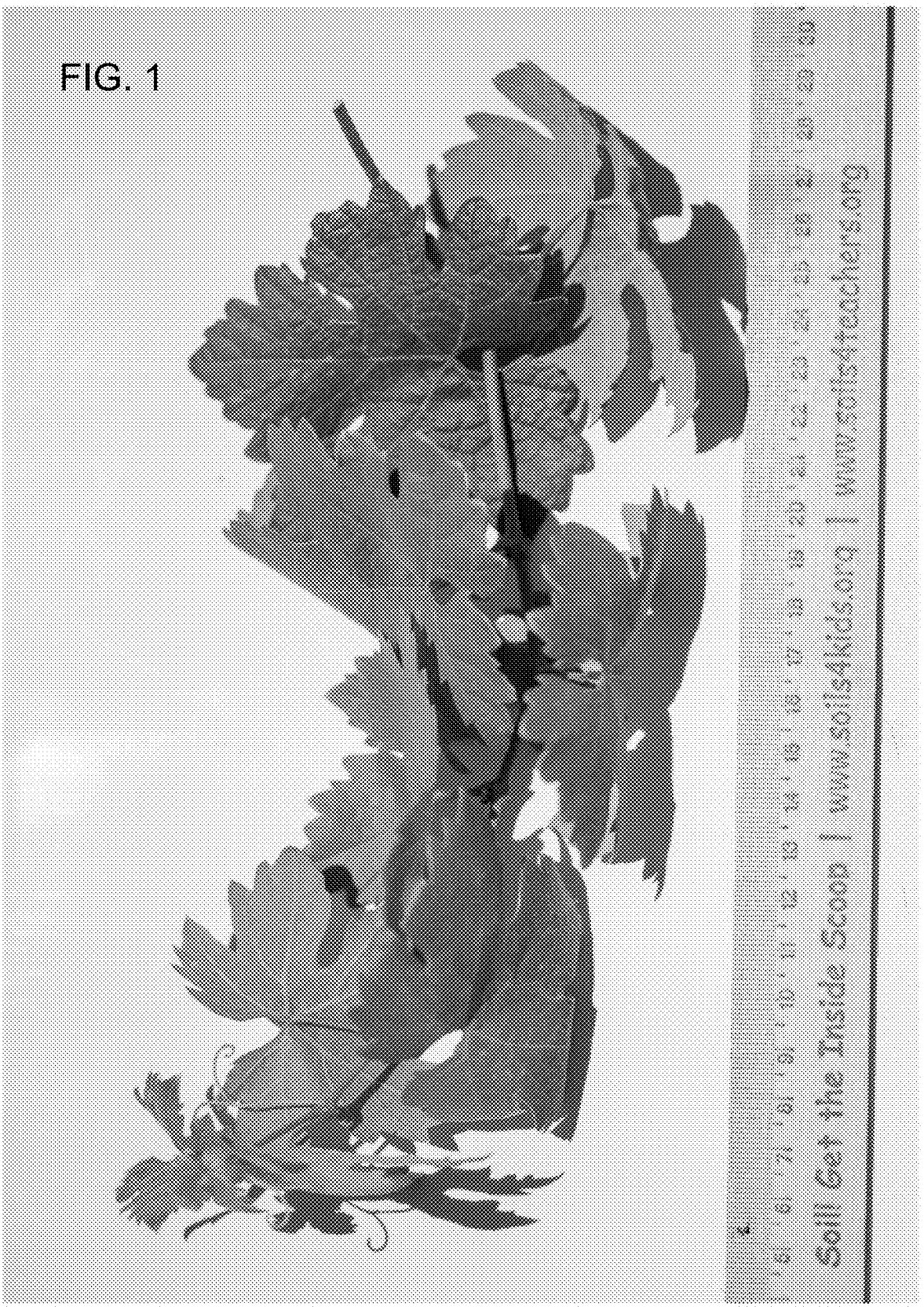
FIG. 1 shows a mature shoot of the plant.
Figure 2:
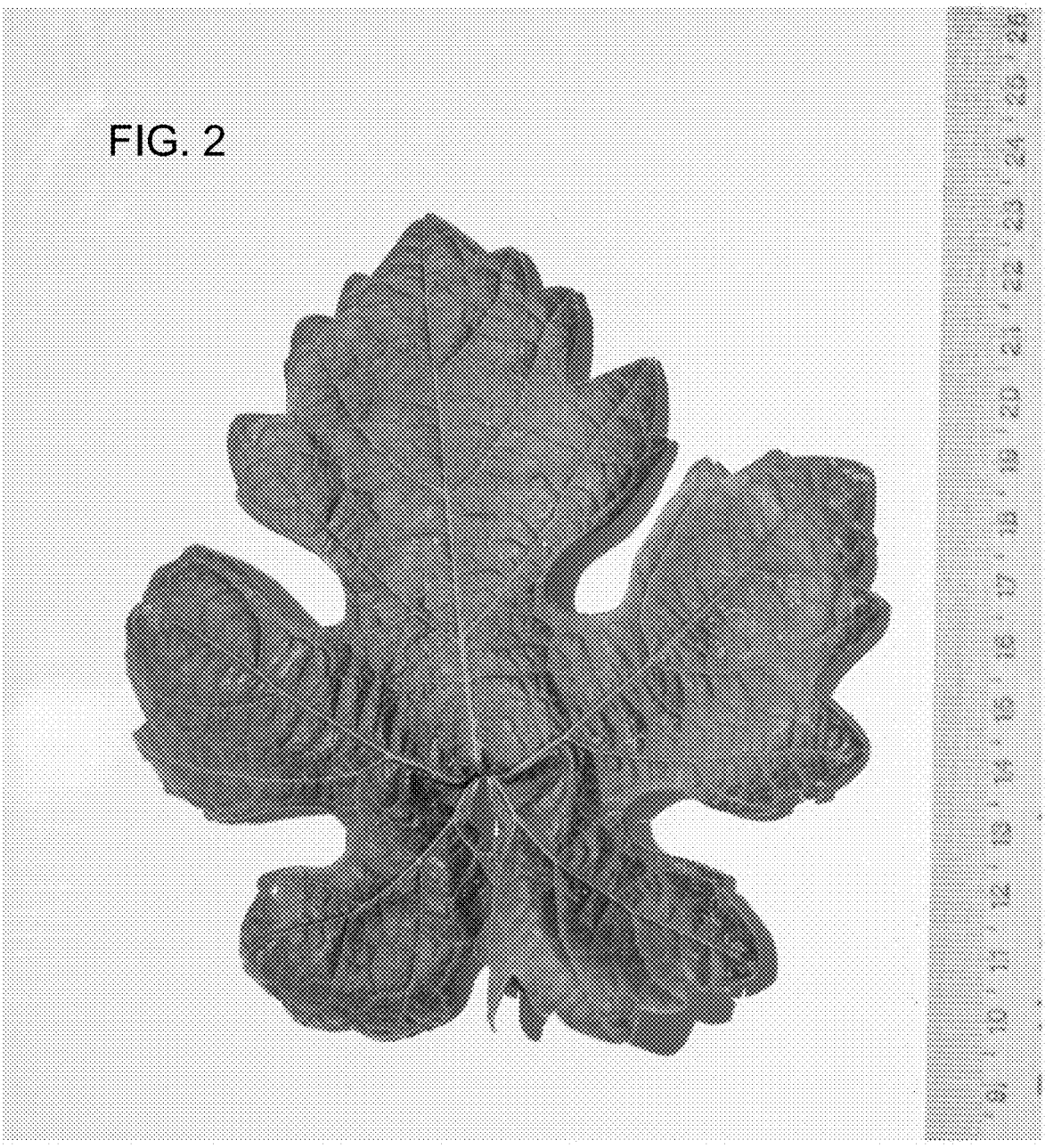
FIG. 2 shows the adaxial surface of a typical leaf.
Figure 3:
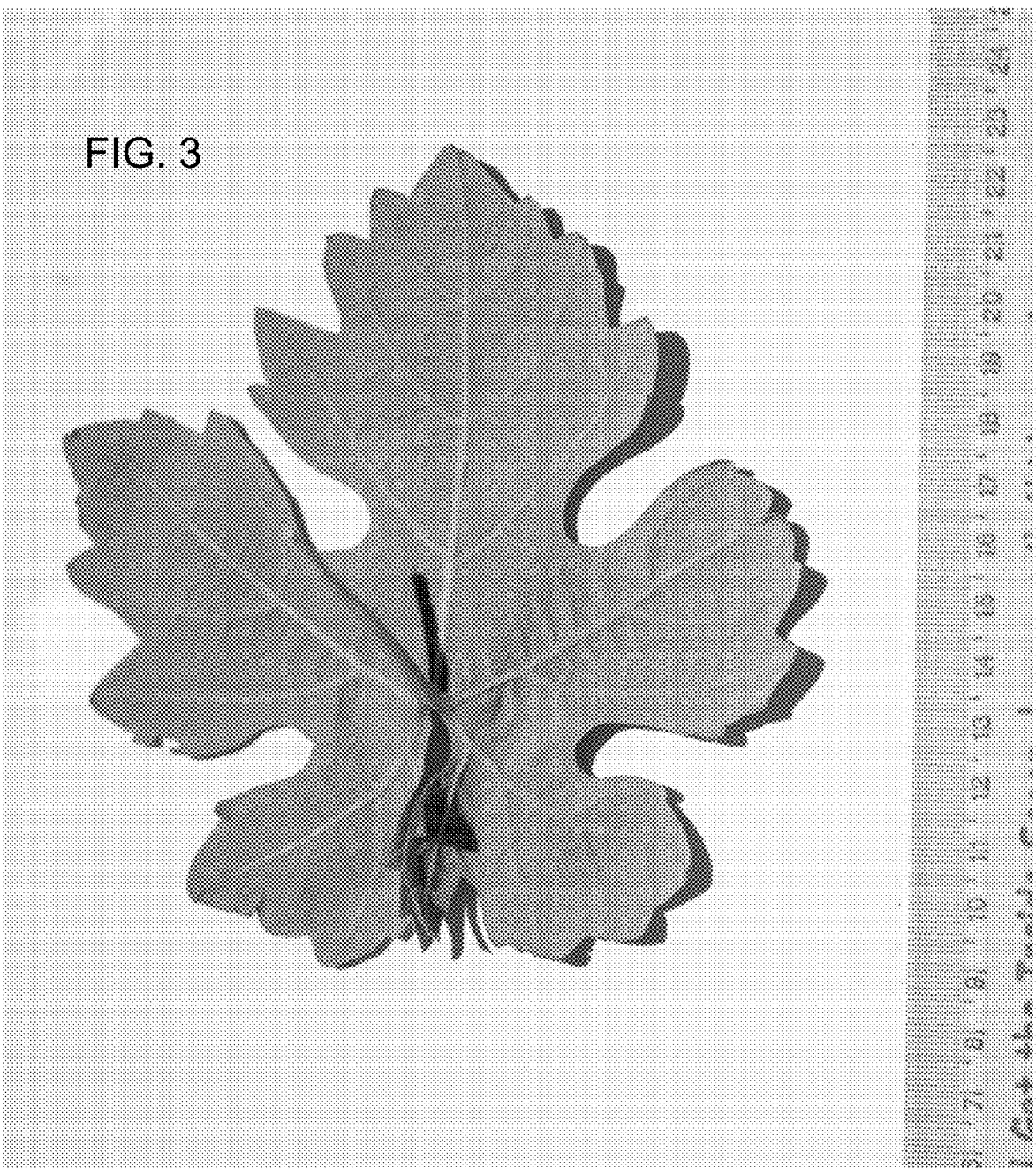
FIG. 3 shows the abaxial surface of the leaf.
Figure 4:
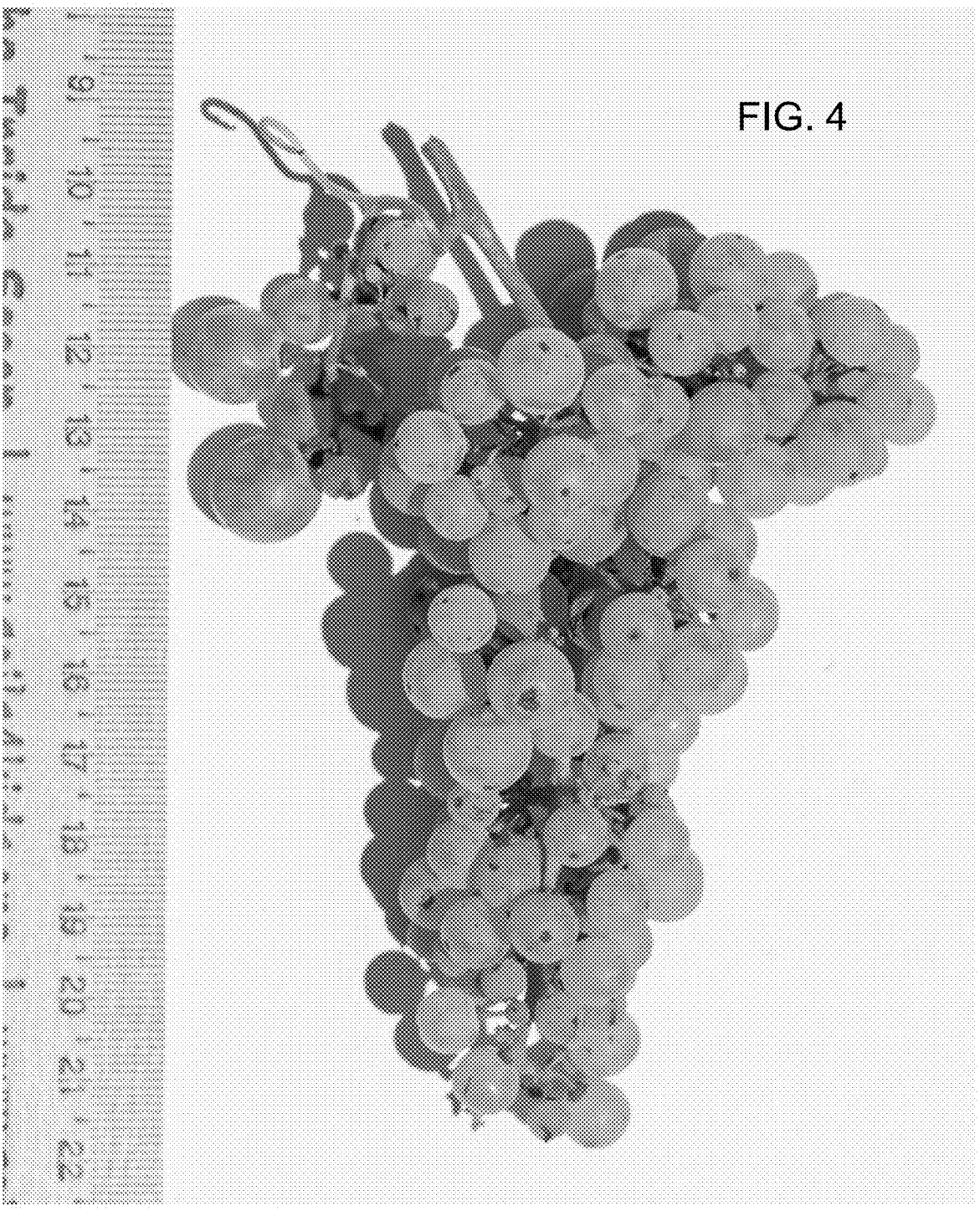
FIG. 4 shows a typical fruit cluster.

The following detailed description of the 'KE-wz1' grapevine plant is based on the originally identified plant, and asexually reproduced progeny grown on a vineyard in Santa Barbara County, California. The plants depicted in the figures are approximately 4 years old, having been propagated from hardwood cuttings taken from the original seedling in 2017 and planted in 2018. Generally, except for the fruit color, the new cultivar closely resembles 'Zinfandel' (not patented).

Certain characteristics of this cultivar may change with changing environmental conditions (e.g., soil type, light, temperature, irrigation, etc.), nutrient availability, or other factors. Listed measurements are expressed as an average of measurements taken from several individual plants of the new cultivar. The first fruit produced was observed in 2017. Color descriptions and other terminology are used in accordance with their ordinary botanical descriptions, unless the context clearly indicates otherwise. Color code designations are by reference to The Royal Horticultural Society Colour Chart (R.H.S.), Sixth Edition (2015).

Small test batches of wine were produced from the initial plantings. The inventor was pleased to find that the fruit accumulated a high level of sugar (in excess of 25 brix) and yet maintained a high level of acidity while expressing aromatic compounds typical of wines described as "aromatic whites."

Vine habit and growth:

*Growth habit*.—Deciduous woody vine with climbing habit via tendrils.

*Vigor*.—Moderate to high vigor, similar to parent 'Zinfandel'.

*Size at maturity*.—Mature vines reach 6-8 feet in height when trained on standard vineyard trellis systems; cane length can extend at least 10-15 feet per growing season if not pruned.

*Trunk diameter*.—Mature trunks (5+ years old) measure 4-6 inches in diameter at 12 inches above ground level.

*Trunk shape*.—Generally cylindrical with irregular surfaces and fissures developing with age.

*Bark texture*.—Mature bark is rough and fissured with peeling layers which is typical of *Vitis vinifera*; young bark is smooth.

*Bark color*.—Mature bark: Greyed-Orange Group, RHS 165A with patches of Greyed-Orange Group, RHS 175B; Young bark: Brown Group, Moderate Yellowish Brown 164B canes.

*Size*.—Mature first-year canes measure 8-12 mm in diameter.

*Internode length*.—6-10 cm average on mature canes.

*Internode width*.—Slightly swollen at nodes to approximately 10-14 mm.

*Node width*.—10-14 mm diameter at widest point.

*Texture*.—Smooth to slightly ridged with visible lenticels.

*Color of mature canes*.—Brown Group, Moderate Brown 165B with occasional streaks of Red-Purple Group, Deep Purplish Red 59B.

*Color of immature shoots*.—Green Group, Moderate Yellow Green 137C with tips showing Red-Purple Group, Deep Purplish Red 59B.

Tendrils:

*Form*.—Bifurcate (branched), intermittently distributed along shoots (typically absent at every third node following the typical pattern of *Vitis vinifera*).

*Size*.—10-15 cm in length, 1-2 mm in diameter.

*Texture*.—Smooth, flexible when young, becoming woody with age.

*Color*.—Green Group, Moderate Yellow Green 137C when young, becoming Brown Group, Moderate Brown 165B when mature.

Bud burst and bloom:

*Bud burst*.—Approximately early April in Santa Barbara County, California (coastal climate, USDA Zone 9b).

*Bloom time*.—Mid to late May in Santa Barbara County, California.

*Duration of bloom*.—Approximately 10-14 days under typical conditions.
*Fruit set*.—Late May to early June.
*Veraison*.—Late July to mid-August in Santa Barbara, California.
*Vendage*.—Mid-August to mid-September in Santa Barbara, California.

Buds:
*Size*.—Dormant winter buds measure 3-5 mm in length, 2-4 mm in width.
*Shape*.—Ovoid to conical.
*Color*.—Brown Group, Moderate Brown 165B with scales showing Greyed-Orange Group, RHS 175B.
*Texture*.—Smooth scales with fine pubescence on outer scales.

Flower size:
*Diameter*.—Individual flowers measure approximately 3-4 mm in diameter.

Petals (calyptra):
*Number*.—5 petals fused at apex forming a cap (calyptra) that falls off during anthesis, as is typical for *Vitis*.
*Length*.—2-3 mm.
*Width*.—Approximately 1 mm at widest point.
*Texture*.—Smooth, thin, membranous.
*Margin*.—Entire (smooth).
*Color* (*exterior surface*).—Green Group, Moderate Yellow Green 137C.
*Color* (*interior surface*).—Yellow-White Group, RHS 158D.

Flower fragrance:
*Fragrance*.—Present but subtle; light, sweet, slightly musky scent typical of *Vitis vinifera* flowers.

Panicle/inflorescence:
*Average number of flowers per panicle*.—150-300 flowers per inflorescence, varying with growing conditions and vine vigor.

Reproductive organs:
*Stigma*.—
*Color*.—Yellow-Green Group, RHS 154C.
*Shape*.—Slightly expanded, capitate.
*Texture*.—Papillate surface for pollen capture.
*Style*.—
*Color*.—Yellow-Green Group, RHS 154C.
*Shape*.—Cylindrical, short (approximately 0.5 mm).
*Ovary*.—
*Color*.—Green Group, Strong Yellow Green 144A.
*Shape*.—Ovoid.
*Measurement*.—Approximately 1-1.5 mm in length.
*Stamen*.—
*Color*.—Yellow-White Group, RHS 158C.
*Length*.—2-3 mm.
*Width*.—Approximately 0.3 mm.
*Anther*.—
*Color*.—Yellow Group, Moderate Yellow 160B.
*Pollen*.—
*Color*.—Yellow Group, Moderate Yellow 160B.
*Production*.—Abundant.

Pollinator information:
*Pollination*.—Self-fertile with perfect flowers (hermaphroditic); does not require a specific pollinator cultivar.
*Pollination mechanism*.—Primarily wind-pollinated, though some insect visitation occurs Leaf arrangement:
*Phyllotaxis*.—Alternate, distichous arrangement along shoots.

Leaf venation:
*Pattern*.—Palmate venation with typically 5 main veins radiating from the petiole attachment point.
*Secondary veins*.—Pinnate branching from primary veins.
*Vein prominence*.—Veins raised and prominent on abaxial surface; slightly depressed on adaxial surface.

Detailed leaf description:
*Shape*.—Deeply 5-lobed, occasionally 3-lobed on weaker shoots; overall outline broadly cordate to orbicular.
*Number of lobes*.—Typically 5 main lobes on mature leaves.
*Apex*.—Each lobe has an acute to acuminate apex.
*Base*.—Deeply cordate with overlapping basal lobes.
*Upper lateral sinuses of mature leaves*.—Deep, U-shaped to V-shaped, extending 40-60% toward the midvein.
*Petiolar sinus*.—Deep, narrow, V-shaped with basal lobes often overlapping.
*Margins*.—Irregularly serrate with sharp, triangular teeth.
*Teeth*.—Pronounced triangular teeth with acute apices; teeth vary in size with larger teeth alternating with smaller teeth.
*Length of teeth*.—3-7 mm.
*Shape of teeth*.—Triangular to narrowly triangular with convex sides.
*Size*.—
*Mature leaf length*.—10-15 cm (excluding petiole).
*Mature leaf width*.—7-10 cm at widest point.
*Texture*.—
*Adaxial surface*.—Slightly bullate (puckered), slightly rough to touch, slightly convex between major veins.
*Abaxial surface*.—Densely tomentose with white to pale gray woolly hairs covering the entire surface.
*Color*.—
*Adaxial surface* (*mature leaves*).—Green Group, Dark Green 36A.
*Adaxial surface* (*immature leaves*).—Green Group, Moderate Yellow Green 137C.
*Abaxial surface*.—Obscured by dense tomentum; underlying surface Green Group, Moderate Yellow Green 137C; tomentum appears White Group, RHS 155D.
*Veins* (*adaxial*).—Green Group, Moderate Yellow Green 137C.
*Veins* (*abaxial*).—Green Group, Moderate Yellow Green 137C, partially obscured by tomentum.
*Petiole*.—
*Length*.—4-8 cm.
*Diameter*.—2-4 mm.
*Color*.—Red-Purple Group, Deep Purplish Red 59B, more intense at junction with leaf blade.
*Texture*.—Smooth to slightly ribbed with fine pubescence.
*Shape*.—Cylindrical with slight groove on adaxial side.

Peduncle/rachis:
*Color*.—Green Group, Moderate Yellow Green 137C when young, becoming Brown Group, Light Brown 164C at maturity.

*Diameter.*—4-6 mm at base of cluster.
*Length.*—3-5 cm from branch attachment to first branching.
*Texture.*—Smooth with fine pubescence.

Berry size and dimensions:
*Average diameter.*—8-12 mm.
*Average length.*—10-14 mm.
*Shape.*—Ovoid to ellipsoid, occasionally slightly oblate.
*Weight.*—Average individual berry weight 1.5-2.5 grams.

Berry detailed characteristics:
*Skin.*—
*Color (immature).*—Yellow Green Group, Moderate Yellow Green 146C.
*Color (mature).*—Yellow Green Group, Strong Yellowish Green N144A with slight translucent quality allowing the greenish-yellow flesh to show through.
*Thickness.*—Thin, approximately 0.3-0.5 mm.
*Texture.*—Smooth, slightly waxy bloom (pruinose) when mature.
*Adherence.*—Skin adheres moderately to flesh; slipskin characteristic absent.
*Flesh.*—
*Color.*—Yellow Group, Brilliant Greenish Yellow 3B.
*Texture.*—Juicy, slightly firm when mature, becoming softer with over-ripening; flesh is described as moderately fine-textured without fibrous elements.
*Consistency.*—Uniform throughout berry.
*Juice.*—
*Color.*—Yellow Group, Brilliant Greenish Yellow 3B to Yellow-White Group, RHS 158C.
*Clarity.*—Slightly cloudy when first crushed, becoming clearer with settling.

Berry flavor and aroma:
*Flavor.*—Sweet when fully ripe with balanced acidity; sugar content typically exceeds 25° Brix at harvest maturity.
*Acidity.*—High, maintaining good acid balance even at high sugar levels (typical pH 3.2-3.4).
*Fragrance.*—Aromatic with floral and citrus notes; described as having characteristics typical of aromatic white wine varieties.
*Taste profile.*—Clean, fruity with hints of citrus, green apple, and subtle floral notes.

Seeds:
*Presence.*—Seeds typically present; usually 1-2 seeds per berry, occasionally 3.
*Size.*—4-6 mm in length, 2-3 mm in width.
*Shape.*—Pyriform (pear-shaped) with pronounced beak.
*Color.*—Brown Group, Moderate Brown 165B.
*Surface.*—Slightly rough with visible chalazal area.

Harvest and ripening characteristics:
*Date of first pick (Santa Barbara County, CA).*—Mid August to early September, depending on seasonal weather variation.
*Date of last pick.*—Mid to late September for optimal fruit quality.
*Date of first fruit ripening.*—Early August (veraison).
*Date of full fruit ripening.*—Late August to early September, typically 90-100 days after bloom.
*Ripening pattern.*—Clusters ripen relatively uniformly; individual berries within a cluster may show slight variation in ripeness.

Market use:
*Primary use.*—Wine production, specifically for high-quality aromatic white wines.
*Characteristics for market.*—The white-skinned fruit allows production of naturally white wine from a Zinfandel-type grape without the need to separate skins before fermentation. The resulting wine maintains Zinfandel's high sugar potential while offering a unique aromatic white wine profile. Suitable for premium varietal white wines, sparkling wine production, and specialty white blends.
*Secondary uses.*—Potential for fresh consumption as table grapes, though primarily cultivated for wine production.

Productivity:
*Fruit yield.*—Moderate to high productivity; mature vines (5+ years) produce approximately 8-12 pounds of fruit per vine under standard vineyard management practices in Santa Barbara County, California.
*Estimated yield per acre.*—Approximately 3-5 tons per acre (based on standard vineyard spacing of 6 feet×8 feet and mature vine production).
*Cluster characteristics.*—Produces moderately compact clusters; average cluster weight 150-300 grams.
*Consistency.*—Productivity is relatively consistent year-to-year under favorable growing conditions.

Environmental tolerances:
*Winter hardiness.*—Cold hardy to approximately 5° F. (−15° C.); similar to standard 'Zinfandel' cultivars. Dormant vines can withstand typical winter temperatures in USDA Zones 7-10.
*Drought tolerance.*—Moderate drought tolerance once established; requires less irrigation than many other *Vitis vinifera* cultivars but performs best with consistent water availability during fruit development.
*Heat tolerance.*—Excellent heat tolerance; thrives in warm to hot summer climates typical of California wine regions. Fruit quality maintained even during extended periods of temperatures exceeding 95° F. (35° C.).
*Climate adaptation.*—Best suited to Mediterranean climates with warm, dry summers and mild winters; performs well in USDA Zones 8-10.

Disease resistance and susceptibility:
*Powdery mildew (Erysiphe necator).*—Shows moderate susceptibility similar to 'Zinfandel'; requires standard fungicide spray programs for commercial production.
*Downy mildew (Plasmopara viticola).*—Moderate susceptibility; benefits from preventative fungicide applications in humid climates.
*Botrytis bunch rot (Botrytis cinerea).*—Lower susceptibility compared to tight-clustered varieties due to moderate cluster density, but can occur in wet conditions near harvest.
*Pierce's disease (Xylella fastidiosa).*—Susceptibility typical of *Vitis vinifera* cultivars; should not be planted in areas with high Pierce's disease pressure without vector management.
*Phylloxera (Daktulosphaira vitifoliae).*—As with all *Vitis vinifera* cultivars, 'KE-wz1' is susceptible to phylloxera and should be grafted onto resistant rootstock in areas where phylloxera is present.
*General observations.*—Overall disease susceptibility profile similar to 'Zinfandel' parent; no unusual disease resistance or susceptibility has been observed. Standard vineyard disease management practices are recommended.

The new cultivar 'KE-wz1' is distinguished from its parent 'Zinfandel' (not patented) primarily by fruit color. While 'Zinfandel' produces dark purple-black berries, 'KE-wz1' produces berries with essentially colorless skins that appear yellowish-green due to the underlying flesh color showing through. This distinction is stable and consistent across multiple seasons and asexual propagations.

In all other vegetative and growth characteristics, 'KE-wz1' closely resembles 'Zinfandel', including:

Leaf morphology (deeply 5-lobed with prominent teeth)
Dense abaxial leaf tomentum
Vine growth habit and vigor
Bloom timing and flower characteristics
Cluster morphology
Berry size and shape
High sugar accumulation potential
Overall environmental adaptations The key distinguishing features of 'KE-wz1' are: Berry skin color: Yellowish-green (RHS N144A) vs. dark purple-black in 'Zinfandel'; Wine production potential: Naturally white wine without skin separation vs. red wine production in 'Zinfandel'; Aromatic profile: Enhanced aromatic white wine characteristics vs. typical red wine profile of 'Zinfandel'

What is claimed is:

1. A new and distinct variety of grapevine plant named 'KE-wz1' as described and illustrated herein.

* * * * *